United States Patent
Kim et al.

(10) Patent No.: US 6,476,204 B1
(45) Date of Patent: Nov. 5, 2002

(54) DEXTRAN-MALEIC ACID MONOESTERS AND HYDROGELS BASED THEREON

(75) Inventors: Sin-Hee Kim, Seoul (KR); Che-Youb Won, Wayne, NJ (US); Chih-Chang Chu, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/743,790

(22) PCT Filed: Aug. 25, 1999

(86) PCT No.: PCT/US99/18818

§ 371 (c)(1),
(2), (4) Date: Jan. 19, 2001

(87) PCT Pub. No.: WO00/12619

PCT Pub. Date: Mar. 9, 2000

Related U.S. Application Data

(60) Provisional application No. 60/098,571, filed on Aug. 31, 1998.

(51) Int. Cl.[7] .................... C07H 15/10; C08B 37/02; A61K 38/16; A61K 31/70; A61K 31/66
(52) U.S. Cl. ..................... 536/18.2; 514/8; 514/25; 514/59; 536/112
(58) Field of Search .................. 514/8, 25, 59; 536/18.2, 112

(56) References Cited

U.S. PATENT DOCUMENTS

| | | |
|---|---|---|
| 4,920,158 A | 4/1990 | Murray et al. ............. 523/111 |
| 5,013,769 A | 5/1991 | Murray et al. ............. 523/111 |
| 5,393,798 A | 2/1995 | Weber ....................... 521/149 |
| 5,527,856 A | 6/1996 | Rhee et al. ................ 525/84.1 |
| 5,541,304 A | 7/1996 | Thompson .................... 536/20 |
| 5,550,178 A | 8/1996 | Desai et al. ................. 524/56 |
| 5,658,592 A | 8/1997 | Tanibara et al. ............ 424/488 |
| 5,700,848 A | * 12/1997 | Soon-Shiong et al. .......... 522/7 |
| 5,717,087 A | 2/1998 | Dalbe et al. ................. 536/32 |
| 5,731,365 A | 3/1998 | Englehardt et al. ......... 523/206 |

OTHER PUBLICATIONS

Kim, S.–H., et al., J. Biomed. Mater. Res. 46, 160–170 (1999).

* cited by examiner

Primary Examiner—Peter O'Sullivan

(57) ABSTRACT

Biodegradable hydrogels are formed by photocrosslinking dextran-maleic acid monoesters in which the average degree of substitution of each glucose unit of each $\alpha$-D-glucopyranosyl of dextran by maleic acid ranges from 0.60 to 1.6 and which have a weight average molecular weight ranging from 40,000 to 80,000 on a dextran basis. The hydrogels at pH 7 have maximum swelling ratios ranging from 500 to 1,500 percent. The hydrogels are characterized by increase in swelling ratio as average degree of substitution increases. The hydrogels are useful, for example, for drug delivery and solubility enhancers of drugs, as protective encapsulators of viruses used in gene therapy, and for conventional uses of hydrogels.

8 Claims, 3 Drawing Sheets

DEXTRAN-MALEIC ACID MONOESTERS AND HYDROGELS BASED THEREON

CROSS-REFERENCE TO RELATED APPLICATIONS

This application is a filing under 35 U.S.C. 371 of PCT/US99/18818 which claims the benefit of U.S. Provisional Application No. 60/098,571, filed on 31 August 1998 and incorporates by reference the entire disclosure of U.S. Provisional Application No. 60/098,571; PCT/US99/18818 has been published under No. WO 00/12619, and the publication is in English.

TECHNICAL FIELD

This invention relates to biodegradable vinyl group containing polymers which are photocrosslinkable into hydrogels.

BACKGROUND OF THE INVENTION

It is recognized that the introduction of vinyl group into water-soluble polymers provides functionality for photocrosslinking into hydrogels. For example, the water-soluble polymers are reacted with acrylates which provide vinyl groups for photocrosslinking reaction. However, the introduction of vinyl groups into the water-soluble polymers has been achieved at the expense of existing hydrophilic groups of the polymers such as hydroxyl or carboxyl groups which contribute to water solubility. As a result, the hydrophilicity of a resulting polymer and its water or solvent solubility are affected by degree of substitution so that water or solvent solubility decreases as degree of substitution increases. Moreover, the swelling ratio of the hydrogels made therefrom decreases as the degree of substitution increases. Therefore, in the prior art, a high degree of substitution is necessary for use of hydrogels for slow release of bioactive compounds and hydrogel use for slow release of bioactive compounds is inconsistent with good solubility of hydrogel forming polymers.

SUMMARY OF THE INVENTION

It is been discovered herein that vinyl-group-containing hydrogel precursors of excellent solubility that provide hydrogels that are useful for slow release of bioactive compounds are provided by monoesters of maleic acid with dextran. By monoester it is meant that the compounds have free carboxyl provided by non-esterifying carboxyl group of maleic acid. In other words, in each attached maleic acid segment, there is one ester group and one vinyl group and one free carboxyl group. The vinyl groups provide functionality for cross-linking into hydrogels. The free carboxyl groups impart hydrophilicity and enhanced solubility and are available for forming ester with and thereby linking to bioactive compound. Thus, the esterification of dextran hydroxyl results not only in addition of unsaturation for cross-linking for hydrogel formation but also in the provision of a free carboxyl group which is more hydrophilic than the dextran hydroxyl which is esterified and increases solubility while providing vinyl group for cross-linking. Contrary to what is disclosed in prior art, the hydrogel precursors have increased solubility with increasing degree of substitution and provide hydrogels with increased swelling ratio as degree of substitution increases. The hydrogel precursors herein are unique in that increase in degree of substitution does not require sacrificing solubility.

One embodiment of the invention herein is directed to dextran-maleic acid monoesters in which the average degree of substitution of each glucose unit of each α-D-glucopyranosyl moiety of dextran by maleic acid ranges from 0.60 to 1.6, preferably from 0.60 to 1.30, for example, from 0.60 to 1.26, and having a weight average molecular weight ranging from 40,000 to 80,000 on a dextran basis.

These compounds are exemplified by the formula

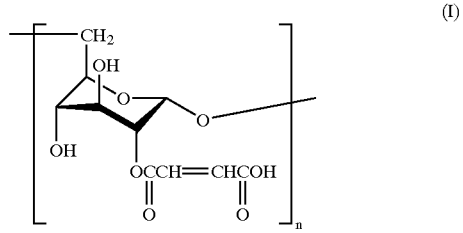

where n has a range providing the above-described molecular weight range, for a degree of substitution of 1.0.

In a subset of this embodiment, the dextran-maleic acid monoesters have an average degree of substitution ranging from 0.85 to 0.95 and a weight average molecular weight ranging from 65,000 to 75,000 on a dextran basis.

In another subset of this embodiment, the dextran-maleic acid monoesters have an average degree of substitution ranging from 1.20 to 1.26 and a weight average molecular weight ranging from 65,000 to 75,000 on a dextran basis.

In another embodiment herein there is provided a biodegradable hydrogel formed by photocrosslinking the aforedescribed dextran-maleic acid mono ester or ester thereof (where the free carboxylic acid group of maleic acid moiety is esterified with a bioactive agent, e.g., a drug to be administered), in solution in an aqueous medium buffered to a pH ranging from 2 to 8, and drying, which at pH 7 has a maximum swelling ratio percentage ranging from 500 to 1,500 and which is characterized by increase in swelling ratio as average degree of substitution increases.

The term "on a dextran basis" is used herein to mean the weight average molecular weight referred to is that of the dextran starting material for preparing the dextran-maleic acid monoester which provides the dextran moiety of the dextran-maleic acid monoester.

The term "hydrogel" is used herein to mean a polymeric material which exhibits the ability to swell in water and to retain a significant portion of water within its structure without dissolution.

The term "biodegradable hydrogel" is used herein to mean hydrogel formed by cross-linking a polymer which is degraded by water and/or by enzymes found in nature.

The term "hydrogel precursor" is used herein to mean water soluble polymer that is photocrosslinkable in solution in a medium to form a hydrogel The term "photocrosslinking" is used herein to mean causing vinyl bonds to break and form cross-links by the application of radiant energy.

The term "degree of substitution" is used herein to mean the number of hydroxyl groups in a glucose unit of α-D-glucopyranosyl moiety of dextran that form ester group with maleic acid. Since each said glucose unit contains three hydroxyl groups, the maximum degree of substitution is 3.0. The average degree of substitution connotes the average degree of substitution based on all the glucose units in the molecules of hydrogel precursor.

The term swelling ratio is a percentage based on the following calculation $$\text{Swelling ratio (\%)} = \frac{W_s - W_o}{W_o} \times 100$$

where $W_s$ is equal to the weight of the swollen hydrogel and $W_o$ is the weight of a dried hydrogel. The swelling is with aqueous solution and the dried hydrogel is dried so as to be dry to the touch.

The term "maximum swelling ratio" (at pH 7) means the maximum swelling ratio obtained in the test set forth in Example VI hereinafter on soaking in pH 7 buffer solution.

DETAILED DESCRIPTION

Figure 1:
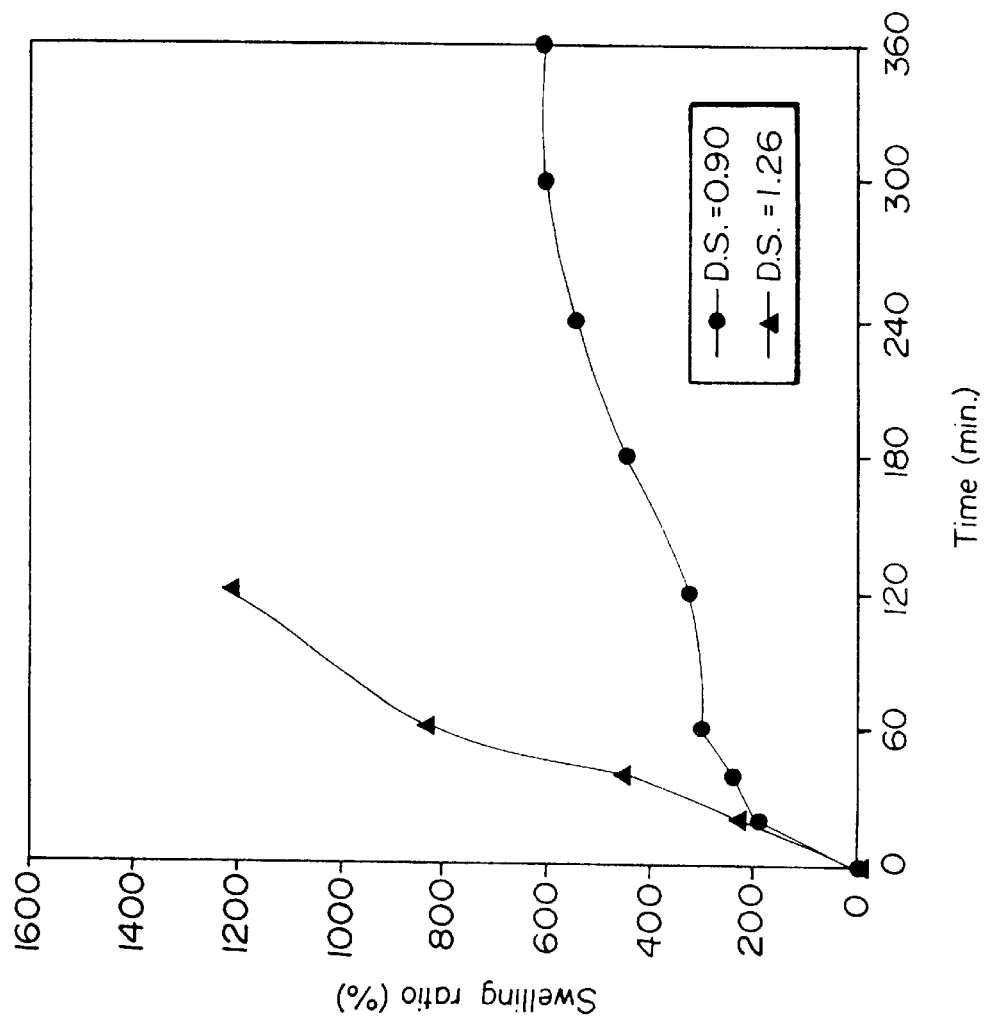
FIG. 1 shows swelling ratios obtained in Example VI after soaking at pH3.

The starting material dextran is dextran having a weight average molecular weight ranging from 40,000 to 80,000 and is commercially available. Dextran is (1→6) linked α-D-glucopyranosyl residues and carries three hydroxyl groups per glucose unit.

The dextran-maleic acid monoester hydrogel precursors of the invention herein are readily prepared by reaction of dextran with maleic anhydride in the presence of a Lewis-base catalyst. The Lewis-base catalyst is to strengthen the nucleophilicity of the hydroxy groups of the dextran. In the reaction, hydroxy group of dextran reacts with maleic anhydride to form an ester linkage; this step leads to a ring opening of the anhydride group of maleic anhydride and generates a free carboxylic acid group at the end of the attached segment.

The reaction of dextran with maleic anhydride is preferably carried out in a dipolar aprotic solvent, e.g., N,N-dimethylformamide (DMF). LiCl is preferably included in the DMF reaction solvent to increase the solubility of dextran in DMF. The LiCl does this by forming a salt with DMF and thereby increasing the polarity of the DMF.

The Lewis-base catalyst is preferably triethylamine (TEA).

The reaction can be carried out, for example, at molar ratio of maleic anhydride to hydroxyl groups of dextran ranging from 0.3:1 to 3.0:1, a molar ratio of triethylamine (TEA) to maleic anhydride ranging from 0.00 1:1.0 to 0.10:1.0, reaction temperatures ranging from 20° C. to 80° C. and reaction times ranging from 1 hour to 20 hours or more. Conditions providing the highest degrees of substitution consistent with efficient use of reagents and time were obtained with a molar ratio of maleic anhydride to hydroxyl groups of dextran of 2:1, a molar ratio of triethylamine to maleic anhydride of 0.05:1, reaction temperature of 60° C. and reaction times of about 10 to 20 hours.

In general, increasing molar ratio of maleic anhydride to dextran hydroxyl, increasing molar ratio of TEA to maleic anhydride and increasing reaction time causes increase in degree of substitution. A close to linear increase in the degree of substitution has been observed as the molar ratio of maleic anhydride to hydroxyl group is increased to 2:1. A further increase in molar ratio to 3:1 resulted in a very small increase in degree of substitution (2%). An increase in molar ratio of catalyst to maleic anhydride was observed to significantly increase the degree of substitution as molar ratio was increased to 0.05:1. Further increase to 0.1:1 produced a small increase in degree of substitution. So far as the influence of reaction temperature is concerned, data indicates a maximum degree of substitution being obtained at a reaction temperature of about 60° C. The esterification reaction was facilitated as reaction temperature was increased from 20° C. to 60° C., but at 80° C., degree of substitution obtained was found to be decreased compared to degree of substitution obtained on reaction at 60° C. The parameter most influencing degree of substitution was found to be molar ratio of maleic anhydride to dextran hydroxyl.

Dextran-maleic acid monoester hydrogel precursor having an average degree of substitution ranging from 0.85 to 0.95 and a weight average molecular weight ranging from 65,000 to 75,000 on a dextran basis can be prepared, for example, by utilizing dextran of said weight average molecular weight as a starting material and reaction conditions of 1 mole of maleic anhydride to 1 mole of dextran hydroxyl, 0.10 moles of TEA to 1 mole of maleic anhydride, reaction temperature of 60° C. and reaction time of 8 hours to produce compound with a degree of substitution of about 0.90 or of molar ratio of maleic anhydride to hydroxyl group of dextran of 1:1, molar ratio of TEA to maleic anhydride of 0.03:1, reaction temperature of 80° C. and reaction time of 20 hours to obtain compound with a degree of substitution of 0.90 or using these results to select other conditions to produce compounds with degrees of substitution in the range of 0.85 to 0.95.

Dextran-maleic acid monoester hydrogel precursors having an average degree of substitution ranging from 1.20 to 1.26 and a weight average molecular weight ranging from 65,000 to 75,000 on a dextran basis can be prepared, for example, by utilizing dextran of said weight average molecular weight as a starting material and reaction conditions of 1 mole of maleic anhydride to 1 mole of dextran hydroxyl, 0.10 moles of TEA to 1 mole of maleic anhydride, reaction temperature of 60° C. and reaction time of 8 hours to obtain compound having degree of substitution of 1.26 or using this result to select other conditions to produce compounds with degrees of substitution in the range of 1.20 to 1.26.

As indicated above, the free carboxyls in the monoesters can be esterified with a bioactive agent, e.g., a drug. Examples of drugs and bioactive agents that may be reacted with free carboxyl of the dextran-maleic acid monoester hydrogel precursors herein to form esters include drugs and other bioactive agents containing one or more hydroxyl groups including, for example, estrone, estradiol, doxorubicin, and camptothecin. The esterifications can be carried out at normal esterification conditions.

The degree of substitution obtained is readily calculated from $^1$H-NMR data by integration and normalization of the double bond in the maleic acid segment and the hydroxyl hydrogen peaks of the dextran segment and dividing the peak area of the double bond region of the maleic acid segment by the peak area of the hydroxyl hydrogen in the dextran.

The degree of substitution to be obtained depends on the end use of the hydrogel. For example, for hydrogel use for drug delivery over a period of ranging from as low as 2 hours to 48 hours or more, a degree of substitution ranging from 0.60 to 1.6 may be considered important. For hydrogel use for encapsulation of viruses used in gene therapy, a degree of substitution ranging from 0.60 to 1.6 may be considered important.

The dextran-maleic acid monoester hydrogel precursors have excellent solubility which is increased compared to the solubility of dextran. This excellent solubility is important because it facilitates reaction with or entrapping or coating of hydrophilic bioactive agents and facilitates hydrogel formation. It does this by minimizing the need for solvents different from water and by minimizing the need for heating to cause dissolution. Like dextran, the dextran-maleic acid monoester hydrogel precursors dissolve to form clear at room temperature in water and dimethylsulfoxide but the dextran-maleic acid monoester precursors dissolve to form clear solutions in water and dimethylsulfoxide faster than dextran does. The solubility in water at room temperature is important because water is present in abundance and is non-toxic. On the other hand, prior art hydrogel precursors are normally not readily soluble in water and require higher temperatures than room temperature for dissolution and/or organic solvents which present purification problems and can result in reduced loading of bioactive agent in hydrogel (since purification can involve washing which incidentally removes some loaded bioactive agent). Moreover, the excellent solubility of the dextran-maleic acid precursors herein provides more homogenous loading of bioactive agent. The dextran-maleic acid monoester hydrogel precursors herein also dissolve to form clear solutions at room temperature in dimethylformamide, diethylacetamide and N-methylpyrrolidone while dextran does not. Neither dextran nor the dextran-maleic acid monoester hydrogel precursors dissolve to form clear solutions at room temperature in tetrahydrofuran or methylene chloride. Thus, the dextran-maleic acid monoester hydrogel precursors have the unique property compared to dextran of being readily reacted with certain drugs and other bioactive compounds, e.g., estrone that dissolves in polar solvents such dimethylformamide, dimethylacetamide, N-methylpyrrolidone and dimethylsulfoxide at room temperature, but dissolves only very slightly in water; isonicotinic acid hydrazide and acetylsalicylic acid which dissolve in dimethylformamide but have limited solubility in water.

We turn now to the embodiment herein directed to a biodegradable hydrogel formed by photocrosslinking the aforedescribed dextran-maleic acid monoester or ester thereof with bioactive agent in a solution of aqueous medium buffered to a pH ranging from 2 to 8, and drying.

In one instance, the aqueous medium in which the precursor is dissolved for photocrosslinking is buffered to a pH of 7. A suitable aqueous medium buffered to pH 7 is available from VWR Scientific Products of West Chester, Pa. under catalog number 3417-115 and contains 0.05M sodium phosphate, dibasic (Chemical Abstract Registry Number 7558-79-4), 0.05M potassium phosphate, monobasic (Chemical Abstract Registry Number 7778-77-0), antimicrobial and water. Lower pH brings the double bonds closer together due to collapse of structure and thereby facilitates the cross-linking reaction.

Preferably, photoinitiator, e.g., 2,2'-dimethoxy-2-phenyl acetophenone, is added to the solution to be subjected to photocrosslinking in an amount of 1 to 5% by weight of the dextran-maleic acid hydrogel precursor being photocrosslinked.

The photocrosslinking is readily carried out by UV irradiation, e.g., using a long wave UV lamp.

Drying is preferably so that the formed hydrogel is dry to the touch.

Drying can be carried out at room temperature in a vacuum oven.

For entrapping of a bioactive agent, the agent may be admixed with the hydrogel precursor in the solution of buffered medium that is exposed to photocrosslinking conditions so that photocrosslinking causes formation of hydrogel with bioactive agent entrapped therein or encapsulated thereby.

The degree of cross-linking obtained depends on the degree of substitution for the precursor. The minimum degree of substitution necessary in the precursor for proper UV photocrossliking was found to be 0.60. Photocrosslinking is carried out to obtain at least the cross-lining producing gelation. The time of photocrosslinking can be prolonged beyond that just obtaining gelation, to obtain more crosslining. The effect of increased degree of cross-linking is to decrease solubility and increase stability.

An example of cross-linking that may be obtained is set forth below

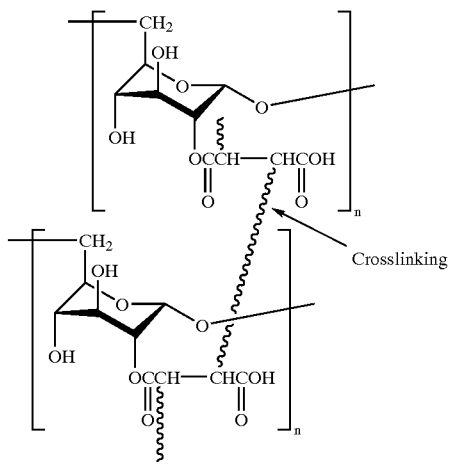

where n has a range providing the above-described molecular weight range, for a degree of substitution of 1.0.

At pH 7, the hydrogel in aqueous medium has a maximum swelling ratio ranging from 500 to 1,500 percent.

The formed hydrogel has a high swelling ratio in aqueous solution with the magnitude of the swelling depending on the pH of the aqueous solution into which a dried hydrogel is immersed. The highest equilibrium swelling ratios are obtained at neutral pH, followed by acidic pH (as represented by pH of 3). At alkaline pH (as represented by pH of 10), the hydrogels dissolved before equilibrium swelling was obtained. A higher swelling ratio gives faster release of chemically reacted or entrapped agent. Thus, selection of pH of swelling medium provides a method of controlling release ratio of chemically reacted or entrapped agent in other than a medical environment. In a medical environment, the pH is that present in the area of the body which the hydrogel contacts.

The formed hydrogel is characterized by increased swelling ratio and solubility with increase in degree of substitution by maleic acid in the hydrogel precursor. Increase in swelling ratio with increased degree of substitution is not achieved by hydrogels from acrylic acid and its derivatives. All current experimental and commercial biodegradable hydrogels exhibit lower swelling ratio and solubility as degree of substitution increases.

Higher swelling ratio gives faster release of agent that is reacted with or entrapped in the hydrogel. A higher swelling ratio gives a more open structure which is closer in structure to that of tissue and is important for tissue contact uses.

Higher swelling ratio is connected with high hydrophilicity which is important for contact lense and wound healing utilities.

Higher swelling ratio also provides better absorption for sanitary uses.

The hydrogels formed by the precursors herein are easy to make due to the ability of the hydrogel precursor to dissolve more easily in common organic solvents including water than conventional hydrogel precursors.

The higher the average degree of substitution in the hydrogel precursor, the less the wet stability of the formed hydrogel, i.e., the less the time the hydrogel will exist in aqueous medium before dissolving.

The formed hydrogels are biodegradable because dextran is biodegradable and the ester bonds are biodegradable.

The hydrogels from the precursors herein are useful for controlled release of drugs. For this utility, the drugs may be reacted with the free carboxyls in the precursors to form covalent bonds between drug and precursor or the drug can be physically encapsulated or entrapped by the precursor. The drug is released by metabolic action on the hydrogel, and the attachment to or entrapment in or encapsulation with hydrogel delays release, for example, for 2 to 48 hours or more.

The hydrogels from the precursors herein are useful as a temporary skin cover, e.g., as a wound dressing or artificial skin. In this case, the hydrogel can advantageously incorporate antimicrobial agent and/or would healing growth factor(s).

The hydrogels from the precursors herein are useful as coatings on surgical implants, for example, as a coating on a vascular graft to reduce thrombogenicity. In the case of anti-thrombogenic function, the hydrogel advantageously may entrap or encapsulate or include anti-clotting agent, e.g., heparin.

The hydrogels from the precursors herein are useful to encapsulate viruses used in gene therapy to protect the viruses from the body's immune system until they reach the site where the genetic alteration is to occur. In conventional gene therapy, virus are injected at the site of prospective incorporation and many injections are required to accommodate for inactivation of viruses. The hydrogels herein protect the viruses so that fewer injections may be utilized.

The hydrogels from the precursors herein are useful for agricultural purposes to coat seeds. The hydrogel coating promotes retention of water during seed germination and promotes oxygen transport via pore structures and may include chemical agents, e.g., pesticides, for delivery to the seeds.

The hydrogels from the precursors herein are useful for the administration of basic fibroblast growth factor (bFGF) to stimulate the proliferation of osteoblasts (i.e., promote bone formation) and to stimulate angiogenesis (development of blood vessels). The pendant free carboxylic acid groups in the precursors herein serve as sites for the ionic bonding of bFGF. The hydrogels incorporating bFGF are applied to bone or blood vessels locally. Upon the biodegradation of the hydrogel, sustained release of bFGF for promoting bone growth and blood vessel formation is obtained. The bonding of the bFGF to the precursors herein protects the bFGF against enzymatic degradation or denaturing so the bFGF can perform its biological functions and occurs because of the bFGF's inherent affinity toward acid compounds.

The hydrogels from the precursors herein are also useful in the cases where hydrogels are conventionally used, e.g., for thickening in foods, for moisture release to plants, for fluid uptake and retention in the sanitary area, as hydrophilic coatings for textile applications, for contact lenses and for separation and diffusion gel in chromatography and electrophoresis.

The invention herein is illustrated by the following examples.

EXAMPLE I

Dextran (2.0 gms) having a weight average molecular weight of 70,000 was disolved in 20 ml dimethylformamide containing 10 weight percent LiCl at 90° C. under nitrogen gas. After the dextran was noted to clearly dissolve, the resulting solution was allowed to cool to reaction temperature. Then triethylamine was added in amount of 0.11 gms and stirring was carried out for 15 minutes. Maleic anhydride (3.626 gms) was added. The molar ratio of hydroxyl groups in dextran to maleic anhydride was 1:1. The molar ratio of triethylamine to maleic anhydride was 0.03:1. The reaction temperature was maintained for 20 hours. Runs were carried out at reaction temperatures of 20° C., 40° C., 60° C. and 80° C. At the conclusion of the 20 hour reaction period, the reaction mixtures were precipitated in cold isopropyl alcohol, washed several times with isopropyl alcohol and dried at room temperature in a vacuum oven. Dextran-maleic acid monoester hydrogel precursor was formed and degree of substitution results are set forth in Table 1 below:

TABLE 1

| Temperature (° C.) | Maleic acid content (%) | Degree of Substitution |
|---|---|---|
| 20 | 10 | 0.30 |
| 40 | 17 | 0.51 |
| 60 | 33 | 0.99 |
| 80 | 30 | 0.90 |

EXAMPLE II

Dextran-maleic acid monoester hydrogel precursor was prepared as in Example I except that reaction was carried out at 60° C. and reaction time was varied with runs being carried out with reaction times of 1, 3, 5, 10 and 20 hours. Degree of substitution results are set forth in Table 2 below.

TABLE 2

| Temperature (° C.) | Maleic acid content (%) | Degree of Substitution |
|---|---|---|
| 1 | 12 | 0.36 |
| 3 | 13 | 0.39 |
| 5 | 19 | 0.57 |
| 10 | 28 | 0.84 |
| 20 | 33 | 0.99 |

EXAMPLE III

Dextran-maleic acid hydrogel monoester precursor was prepared as in Example I except the reaction temperature was 60° C., the reaction time was 10 hours and the molar ratio of triethylamine to maleic anhydride was varied with run being carried out at molar ratios of triethylamine to maleic anhydride of 0.01:1.0, 0.03:1.0, 0.05:1.0 and 0.10:1.0. Degree of substitution results are set forth in Table 3 below:

TABLE 3

| Molar ratio | | Maleic acid content (%) | Degree of Substitution |
|---|---|---|---|
| [Maleic anhydride] | [Triethylamine] | | |
| 1.0 | 0.01 | 26 | 0.78 |
| 1.0 | 0.03 | 28 | 0.84 |
| 1.0 | 0.05 | 37 | 1.11 |
| 1.0 | 0.10 | 38 | 1.14 |

EXAMPLE IV

Dextran-maleic acid hydrogel monoester precursor was prepared as in Example I except that the molar ratio of triethylamine to maleic anhydride was 0.10:1, the reaction temperature was 60° C. and the reaction time was 8 hours and the molar ratio of maleic anhydride to hydroxyl groups of dextran was varied with runs being carried out at molar ratios of maleic anhydride to hydroxyl groups of dextran of 0.5:1.0, 1.0:1.0, 1.5:1.0, 2.0:1.0 and 3.0:1.0. Degree of substitution results are set forth in Table 4 below:

TABLE 4

| Molar ratio | | Maleic acid content (%) | Degree of Substitution |
|---|---|---|---|
| [Hydroxyl group] | [Maleic Anhydride] | | |
| 1.0 | 0.5 | 20 | 0.60 |
| 1.0 | 1.0 | 30 | 0.90 |
| 1.0 | 1.5 | 42 | 1.26 |
| 1.0 | 2.0 | 49 | 1.47 |
| 1.0 | 3.0 | 51 | 1.53 |

EXAMPLE V

Solubility testing of dextran-maleic acid monoester hydrogel precursor and dextran were carried out at room temperature in water, dimethylformamide, dimethylsulfoxide, dimethylacetamide, N-methyl pyrrolidone, tetrahydrofuran, and methylene chloride according to the following procedure: 0.1 g of hydrogel precursor was admixed in 5 ml of solvent and stirring was carried out for 24 hours. Runs were carried out with dextran-maleic acid monoester hydrogel precursor prepared from dextran having a weight average molecular weight of 70,000 in one case with a degree of substitution of 0.30 and in other cases with degrees of substitution of 0.90 and 1.26. The dextran tested had a weight average molecular weight of 70,000. The results were the same for the dextran-maleic acid monoester hydrogel precursors regardless of the degree of substitution. The solubility results are set forth in Table 5 below where "+" means dissolves to form a clear solution at room temperature and "−" means does not dissolve to form a clear solution at room temperature.

TABLE 5

| Solvent | Dextran | Dextran - maleic acid |
|---|---|---|
| Water | + | + |
| Dimethylformamide | − | + |
| Dimethylsulfoxide | + | + |
| Dimethylacetamide | − | + |
| N-methylpyrrolidone | − | + |

TABLE 5-continued

| Solvent | Dextran | Dextran - maleic acid |
|---|---|---|
| Tetrahydrofuran | − | − |
| Methylene chloride | − | − |

While both dextran-maleic acid monoesters and dextran were found to dissolve in water and dimethylsulfoxide to form clear solutions at room temperature, dissolution occurred faster for the dextran-maleic acid monoesters than for dextran.

EXAMPLE VI

In one case dextran-maleic acid hydrogel precursor having a degree of substitution of 0.90 (from dextran having a weight average molecular weight of 70,000) and in another case dextran-maleic acid hydrogel precursor having a degree of substitution of 1.26 (from dextran having a weight average molecular weight of 70,000) were dissolved in a pH 7 buffer solution (VWR Scientific Products Catalog No. 34170-115 described above). In each case, the following procedure was used: 0.4 grams of precursor were dissolved in 1 ml buffer solution. Then 2,2'-dimethoxy-2-phenyl acetophenone photoinitiator (3% by weight of the dextran-maleic acid monoester hydrogel precursor) dissolved in 0.024 ml N-methyl pyrrolidone, was added, and rapid stirring was carried out for a few seconds. The resulting solution was poured onto a glass plate and irradiated with a 360-nm long wave UV lamp (UVL-18, UVP Upland, Calif., USA) until gelation occurred. Irradiation was continued for 4 hours and 20 minutes after gelation occurred, for a total irradiation time of 5 hours. The resulting hydrogels were flexible and semi-transparent. The resulting hydrogels were washed several times with isopropyl alcohol and dried at room temperature in a vacuum oven so they were dry to the touch. The dried hydrogel had a brown sticky gum-like appearance and character.

Figure 2:
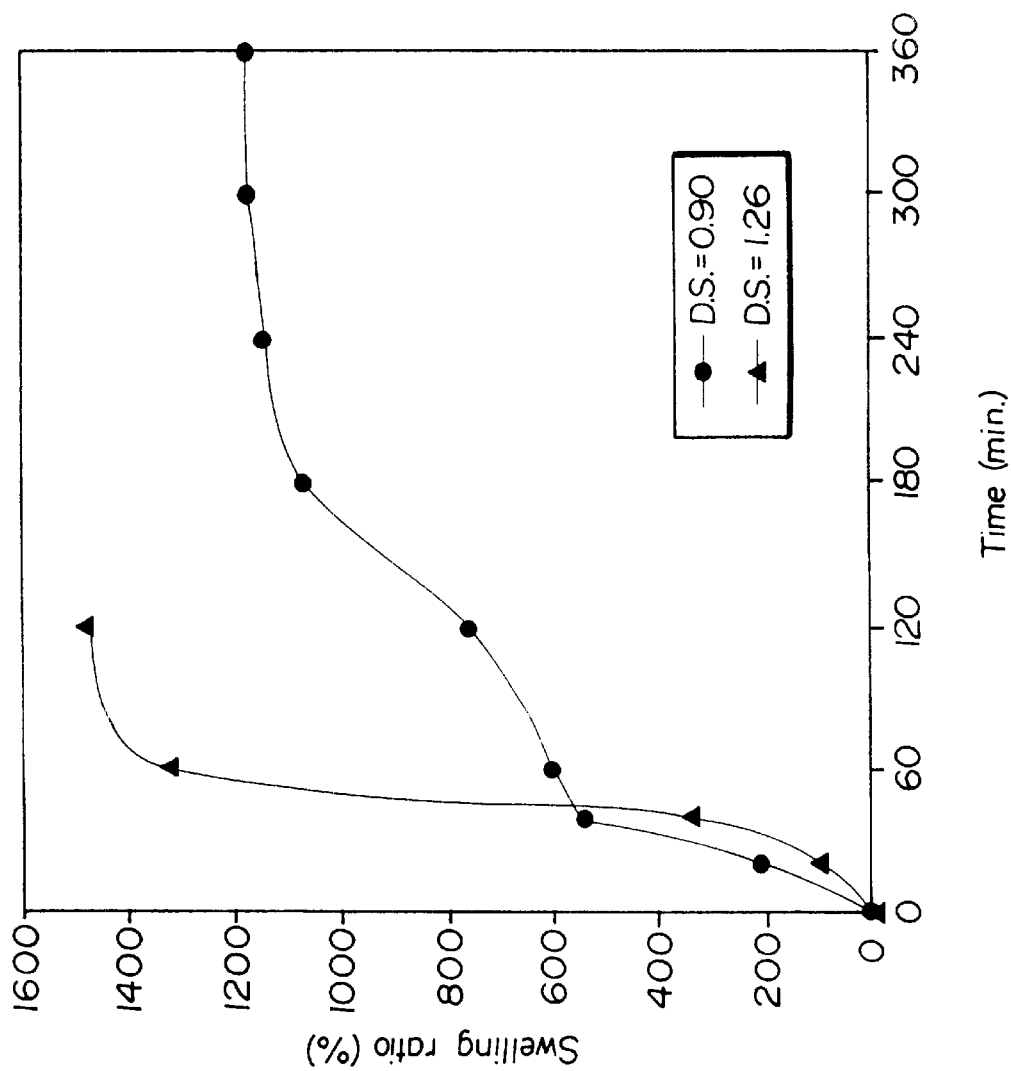
FIG. 2 shows swelling ratios obtained in Example VI after soaking at pH7.
Figure 3:
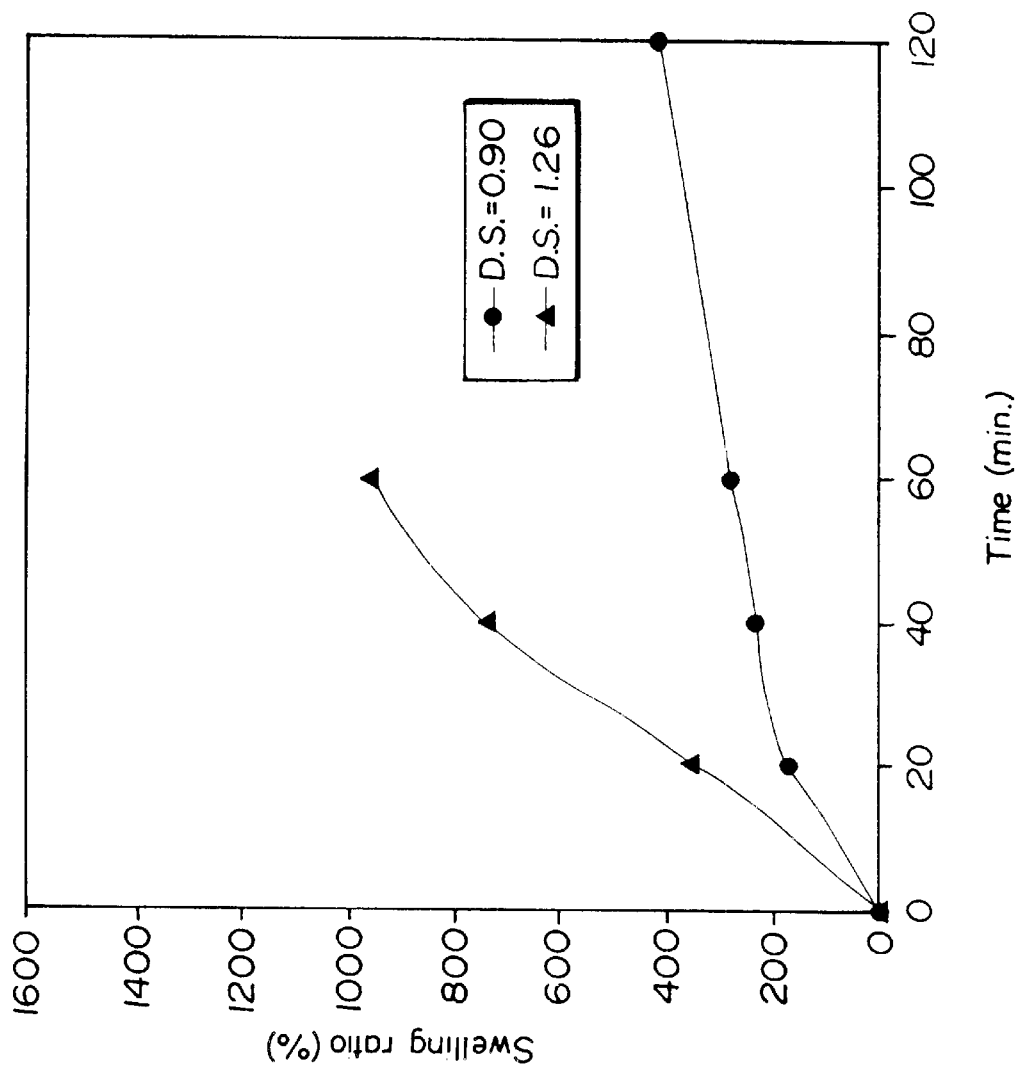
FIG. 3 shows swelling ratios obtained in Example VI after soaking at pH10.

Swelling testing was carried out on the dried hydrogels by the following procedure. Dried dextran-maleic acid monoester hydrogels were weighed and then soaked in buffer solutions. Runs were carried using buffer solution of pH 3 (Catalog No. 34170-103 from VWR Scientific Products of West Chester, Pa. consisting of 0.05M potassium hydrogen phthalate, Chemical Abstracts Registry No. 877-24-7, and anti-microbial in water), using buffer solution of pH 7 (VWR Scientific Products Catalog No. 34170-115 described above), and using buffer solution of pH 10 (Catalog No. SB1 16-500 of Fischer Chemical, Fisher Scientific, Fair Lawn, N.J. consisting of a 0.05 M solution of potassium hydroxide, CAS 1310-58-3, potassium carbonate, CAS 584-08-7, potassium tetraborate, pentahydrate, CAS 1228-83-5, and disodium ethylene diamine tetraacetic acid dihydrate, CAS 6381-92-6, in water). In each case, soaked hydrogel was removed at predetermined intervals, the surface water of the hydrogel was gently removed by a paper towel, and the hydrogel was then weighed until no further weight change was detected. Swelling ratio percentages were calculated using the formula set forth above. The results are set forth in FIGS. 1, 2 and 3, wherein FIG. 1 gives swelling ratios after soaking in solution of pH 3, FIG. 2 gives swelling ratios after soaking in solution of pH 7, and FIG. 3 gives swelling ratios after soaking in solution of pH 10. In each of the figures, "D.S." stands for "degree of substitution." For hydrogel from dextran-maleic acid monoester with a degree of substitution of 0.90, equilibrium swelling was obtained in buffer solution of pH 7 after 5 hours (1,171%) and continued without any sign of structural disintegration for a few days and equilibrium swelling was obtained in a buffer solution of pH 3 after 300 minutes (600%), and this swelling ratio continued until, starting at 48 hours after immersion, the hydrogel started to dissolve.

EXAMPLE VII

Processing was carried out as recited in Example VI in an attempt to obtain hydrogels with dextran-maleic acid monoesters with degrees of substitution of 0.30, 0.36, 0.39, 0.51, 0.57, 0.60 and 0.84. It was found that the minimum degree of substitution required for proper UV-photocrosslinking for a hydrogel was 0.60.

EXAMPLE VIII

Swelling testing was carried out as set forth in Example VI on hydrogels formed from dextran-maleic acid monoesters with degrees of substitution of 0.90, 1.26, 1.47, and 1.53. The hydrogels formed from monoesters of degrees of substitution of 0.90 and 1.26 persisted in buffer solutions (pH 3, 7 and 10) for at least 60 minutes. The hydrogels formed from the monoesters with degrees of substitution of 1.47 and 1.53 showed large water uptake instantly when immersed in buffer solutions (pH 3, 7 and 10) but dissolved shortly thereafter (within 10 minutes) in the buffer solutions.

EXAMPLE IX

Dextran-maleic acid hydrogel precursors having a degree of substitution of 0.90 (from dextran having a weight average molecular weight of 70,000) and having a degree of substitution of 1,26 (from dextran having a weight average molecular weight of 70,000) are used.

In each case, 0.2 gram of dextran-maleic acid hydrogel precursor is dissolved in 1 ml phosphate buffer solution (PBS) of pH 7.4. Then 0.004 gram of 2,2'-dimethoxy-2-phenyl acetophenone is added as an initiator. Then 50 μg bFGF is added. The resulting solutions are poured onto a Teflon slab and irradiated by a long wave UV lamp for 4 hours to obtain cross-linked dextran-maleic acid hydrogel network with bFGF impregnated therein. The hydrogel network is dried under vacuum for two days. The resulting product may be locally applied to bone to promote bone growth, and to blood vessels to promote blood vessel formation.

Variations

Many variations of the above will be obvious to those skilled in the art. Thus, the invention is defined by the claims.

What is claimed is:

1. Dextran-maleic acid monoesters in which the average degree of substitution of each glucose unit of each α-D-glucopyranosyl of dextran by maleic acid ranges from 0.60 to 1.6 and which have a weight average molecular weight ranging from 40,000 to 80,000 on a dextran basis.

2. The dextran-maleic acid monoesters of claim 1, having an average degree of substitution ranging from 0.60 to 1.30.

3. The dextran-maleic acid monoesters of claim 1 having an average degree of substitution ranging from 0.60 to 1.26.

4. The dextran-maleic acid monoesters of claim 1, having an average degree of substitution ranging from 0.85 to 0.95 and a weight average molecular weight ranging from 65,000 to 75,000 on a dextran basis.

5. The dextran-maleic acid monoesters of claim 1, having an average degree of substitution ranging from 1.20 to 1.26 and a weight average molecular weight ranging from 65,000 to 75,000 on a dextran basis.

6. Biodegradable hydrogel formed by photocrosslinking dextran-maleic acid monoester of claim 1 or ester thereof with bioactive agent in solution in a medium buffered to a pH ranging from 2 to 8 and drying, which at pH 7 has a maximum equilibrium swelling ratio percentage ranging 500 to 1,500 and which is characterized by increase in swelling ratio as average degree of substitution increases.

7. The biodegradable hydrogel of claim 6, wherein the dextran-maleic acid monoester has an average degree of substitution not exceeding 1.26.

8. The biodegradable hydrogel of claim 6, wherein the medium is buffered to a pH of 7.

* * * * *